US006296838B1

United States Patent
Bindra et al.

(10) Patent No.: US 6,296,838 B1
(45) Date of Patent: Oct. 2, 2001

(54) ANTI-FUNGAL HERBAL FORMULATION FOR TREATMENT OF HUMAN NAILS FUNGUS AND PROCESS THEREOF

(75) Inventors: Rattan Lal Bindra; Anil Kumar Singh; Abdul Sami Shawl; Sushil Kumar, all of Lucknow, Uttar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/535,514

(22) Filed: Mar. 24, 2000

(51) Int. Cl.[7] .............................. A61K 7/04; A01N 25/00
(52) U.S. Cl. .......................... 424/61; 424/405; 514/772.3
(58) Field of Search .................. 424/61, 405; 514/772.3

(56) References Cited

U.S. PATENT DOCUMENTS 5,653,984 * 8/1997 Fodor et al. ..................... 424/195.1

* cited by examiner

Primary Examiner—Thurman K. Page
Assistant Examiner—S. Howard
(74) Attorney, Agent, or Firm—Darby & Darby

(57) ABSTRACT

The invention relates to an antifungal composition for the treatment of human nails containing extracts of walnut hull, pulverized roots of *Nardostachys jatamansi* or *Vetiveria zizanioides* or *Catharanthus roseus,* polyols, fixed oil, non-ionic emulsifiers, thickening agent plasticizer and base. The invention also relates to a process for the preparation of the above synergistic composition.

6 Claims, No Drawings

ANTI-FUNGAL HERBAL FORMULATION FOR TREATMENT OF HUMAN NAILS FUNGUS AND PROCESS THEREOF

FIELD OF THE INVENTION

The present invention relates to an anti-fungal herbal formulation for treatment of human nails infected with fungus and a process for preparation of such herbal formulation.

The formulation is also useful for prevention of fungal infections in nails and is useful in ensuring that new growth of nails is free from fungal infections.

BACKGROUND OF THE INVENTION

Wet floors, unclean play grounds, common bath showers unclean bathtubs are breeding ground for dermatophytes, that cause athletes foot and nail infection. Dermatophytes have ability to invade keratinized tissue (skin, hair, nails) but are usually restricted to non living cornified layers of the epidermis because of their inability to penetrate viable tissue of immunocompetent host. The invasion ranges from mild to severe infection. The causative dermatophytes of nail infection are *Trichophyton rubrum* or *Tmenta grophytes* or candida. The nail becomes discoloured and thickens. The thickened nail plate then rises and separates from the nail bed. Fungal infection of the nails besides being a cosmetic problem also has significant psychological, physical and social implications. The incidence of infection of the nail has been on the rise in recent years and is usually treated by topical agents like creams and ointments, which are preferably applied before retiring and are gently massaged into the base of the nail and cuticle.

The management of fungal infection of the nails is carried out by chemical and surgical approach. The formulations available for topical application in form of cream or lotions contain benzoic acid, salicylic acid, imidazole, gresofulvin, zinc undecenoate. Oral supplements such as oral gresofulvin and terbinafine are also recommended.

Topical application based on benzoic acid, salicylic acid and zinc undecenoate has been found to require long term application for four to ten weeks. However, despite this, the recovery is not complete and cases of recurrence have been reported. Moreover, the use of benzoic acid can cause hypersensitivity reactions and is also known to be an irritant to skin, eyes and mucous membrane. Oral grisofulvin and terbinafine hydrochloride supplemented by its topical application has the success rate of 40 to 50 percent but the studies on animal have the evidence that grisofulvin causes toxic effects on liver, thyroid and teratogenicity. Use of terbinafine (5%) both orally and topically, achieves penetration of the keratinizing tissues and success rate is reported to be upto 80 percent. However, common the adverse effects following oral administration are gastrointestinal disturbances, nausea, diarrhoea and headache. Topical reaction causes skin reactions and these adverse effects make the use of this preparation limited.

The present invention improves the drawbacks of the available formulation in the market. The invented formulation is based upon the plant products having synergistic effect hence enhancing the anti-fungal activity with negligible side effects or toxicity. The formulation contains extract from the hulls of *Juglans regia*. *Juglans regia* (walnut tree) produces nuts (fruits) covered by green hulls. The green hulls separated from mature walnut contain 50 mg percent of Juglone as reported in paper "Some phytochemical characteristic of *Juglans regia*, E. Leinberkovics; E. Hethelyi; E. Hetesi; Acta. Pharm. Hung., 1987, V. 57(3–4), 133–142. Besides juglone, it contains 0.4 to 0.8 percent ascorbic acid. Juglone a simple nethoquinone (5-hydroxy-1,4-nethoquinone) has a moderate antifungal activity as reported in paper "Antimicrobial activity of Juglone. A M Clark; T M Jurgens; C D Hufford. Phytotherpy Research. 1990, 4(1), 11–14.

In the paper "Herbal antifungal cream" M V Devi; A. Suneeta, Journal of Research and Education in Indian Medicine. 1993. 12(1), 1–3 (India), dry extracts of whole nut of *Juglans regia* and *Prunus communis* have been reported to have antifungal activity against Aspergillus species.

OBJECTS OF THE INVENTION

The main object of the present invention is to provide an anti-fungal herbal formulation for treatment of human nails infected with fungus Another object of the present invention is to provide an anti-fungal herbal formulation for treatment of human nails infected with fungus, which does not cause any sensitizing effect when applied topically on nails.

Another object of the present invention is to provide an anti-fungal herbal formulation useful for protecting the nails against fungal infections, also to keep the new growth of nails free from infections.

Yet another object the present invention is to provide an anti-fungal herbal formulation having a mild keratolytic effect so that it will reach down below the upper bed to lower bed of the nail to prevent infection and the recurrence of the infection.

Another important object of the present invention is to provide a process for the preparation of an anti-fungal herbal formulation useful for treatment of infected human nails, protecting the nails against fungal infections, also to keep the new growth of nails free from infections.

SUMMARY OF THE INVENTION

Accordingly the present invention provides an antifungal composition for the treatment of human nails which comprises from 10–15% extract of walnut hull in acetone or alcohol or butanol wherein Juglone (extract of walnut hull) has been partially fractionated, 20 to 30% of pulverized roots of *Nardostachys jatamansi* or *Vetiveria zizanioides* or *Catharanthus roseus,* 5–10% of polyols selected from propylene glycol or polyethylene glycol or ethylene glycol, 5–10% of fixed oil selected from sesame oil, mustard oil, linseed oil 5–10%, 10–15% of non-ionic emulsifiers selected from stearic acid or lanolin or vegetable wax, 15–20% of plasticizer selected from polyvinyl acetate or amyl acetate or food grade gelatin and 20–25% of base selected from nitrocellulose, kaolin or talc.

The present invention also provides a process for the preparation of an antifungal composition for the treatment of human nails which comprises, from 10–15% extract of walnut hull in acetone or alcohol or butanol wherein Juglone has been partially fractionated, 20 to 30% of pulverized roots of *Nardostachys jatamansi* or *Vetiveria zizanioides* or *Catharanthus roseus,* 5–10% of polyols selected from propylene glycol or polyethylene glycol or ethylene glycol, 5–10% of fixed oil selected from sesame oil, mustard oil, linseed oil 5–10%, 10–15% of non-ionic emulsifiers selected from stearic acid or lanolin or vegetable wax, 15–20% of plasticizer selected from polyvinyl acetate or amyl acetate or food grade gelatin and 20–25% of base selected from nitrocellulose, kaolin or talc, said process comprising (a)

washing the walnut hulls of *Juglan resia* with water, air drying and extracting the said hulls at ambient temperature with acetone, butanol or alcohols, (b) making the extract solvent free by any known method and partially fractionating the said extract by chilling, (c) washing the roots of *Nardostachys jatamansi* or *Vetiveria zizanioides* or *Catharanthus roseus* with water and air drying and powdering the said roots to ≦80 microns to get pulverised material, (d) heating a thickening agent selected from polyvinyl acetate, food grade gelatin and amyl acetate at a temperature of up to 80° C., (e) adding a base selected from nitrocellulose, kaolin or talc for filling by stirring, and (f) adding a fixed oil selected from sesame oil, mustard oil, linseed oil and a polyol selected from propylene glycol or polyethylene glycol or ethylene glycol to the solution from step (e).

The plasticizers are melted at about 80° C. and emulsifier is added followed by the addition of the base selected from kaolin or talc or nitrocellulose and thoroughly stirred. Thereafter, polyol and fixed oils are added. Pulverized root material is added and slowly stirred so that a homogeneous emulsion is formed and extract from walnut hull is added and stirred with a controlled stirring motion at a temperature of 35–40° C.

In an embodiment of the present invention, the walnut hull extract may be extracted using, acetone, alcohol, or butanol as solvents.

In another embodiment of the invention, the pulverized roots are selected from *Nardostachys jatamansi Vetiveria zizanioides, Catharanthus roseus*.

In another embodiment of the invention, the polyols may be selected from propylene glycol, polyethylene glycol or ethylene glycol.

In yet another embodiment of the invention, the emulsifier is selected from stearic acid, vegetable wax or lanolin in a base of kaolin, nitrocellulose or talc.

DETAILED DESCRIPTION OF THE INVENTION

The main aim of the present invention is to formulate a fungitoxic cream for prevention, cure and non-recurrence of fungal infection on human nails without any irritation or toxic effects. The cream is formulated on *Juglans regia* (walnut) hulls extract. Hulls are a waste product while cleaning the nuts. The solvent free extract of walnut hulls in acetone, alcohol or butanol when applied on nails of human subjects having mild to severe fungal infection shows very poor efficacy even on prolonged treatment on the healing and fungitoxic effect. The incidence of recurrence of infection is also common. However, the applicants have surprisingly found that when an extract containing juglone is synergised with powdered roots of *Vetiveria zizanioides, Catharanthus roseus,* or *Nardostachys jatamansi* it exhibits unexpected properties in terms of cure and prevention of fungal infections. The extract of Catharanthus is used as anticancer, and essential oil from Vetiver and *jatamansi* are used in food flavours and perfumery industry. The synergistic effect is responsible not only for the curing of the fungal infection but also prevention of its recurrence. In addition, since the formulation is based on natural botanical extracts, it does not produce any sensitizing effect on application.

The base material, i.e., nitrocellulose/amyl nitrate/food grade gelatin with non-ionic emulsifies allows the formulation to adhere to the nails while linseed oil helps in drying of the formulation on nails after its application.

The formulation of the present invention is not a mere admixture resulting in mere aggregation of properties of the individual ingredients but a synergetic composition having improved and unexpected properties. It is believed that the improved properties are due to synergism wherein the basic ingredient juglone from *Juglans regia* hull extract is made fully functional resulting in complete fungitoxic activity and prevention of recurrence of fungal infections of the nails.

The present invention will be described with reference to the following illustrative and non-limitative examples:

EXAMPLE 1

| | |
|---|---|
| Extract of Juglans regia (Walnut) hulls (in acetone/alcohol/butanol) | 10% |
| Powdered Nardostachys jatamansi roots (granulometry ≦ 80 microns) | 25% |
| Ethylene glycol | 5% |
| Mustard Oil | 5% |
| Vegetable wax | 10% |
| Polyvinyl acetate | 20% |
| Talc | 25% |

Walnut hulls from (*Juglans regia*) are washed with water and air-dried, powdered and extracted at ambient temperature with acetone or butanol or alcohol. The extract is made free of solvent and partially fractionated by chilling. *Nardostachys jatamansi* roots are washed with water, air dried and powdered to ≦80 microns.

Polyvinyl acetate is heated over a steam bath to 80° C. and talc is added and stirred so that mixing is complete. Mustard oil and ethylene glycol is added and stirred vigorously, followed by the addition of vegetable wax. Stirring is controlled and temperature is reduced to 60° C. Thereafter, powdered *Nardostachys jatamansi* of ≦80 microns is added. When mixing is complete extract of *Juglans regia* (walnut) hulls is added and mechanically stirred with a controlled stirring motion and temperature is set between 35–45C. The composition is seen to be uniform.

The formulation was applied on ten human subjects having fungal nail infection the fungitoxic effect started after four day and the complete recovery was observed after ten days without any side effects.

EXAMPLE 2

| | |
|---|---|
| Extract of Juglans regia (Walnut) hulls (in acetone/alcohol/butanol) | 10% |
| Powdered Catharanthus roseus roots (granulometry ≦ 80 microns) | 25% |
| Propylene glycol | 5% |
| Sesame Oil | 5% |
| Stearic acid | 10% |
| Gelatin (food grade) | 20% |
| Kaolin | 25% |

Extract of *Juglans regia* and powder of Catharanthus roots was prepared as described in Example No. 1. Gelatin and stearic acid were melted at 80° C. over a steam bath. After adding kaolin the mixture was thoroughly stirred and propylene glycol and sesame oil were added followed by addition of powdered *Catharanthus roseus* roots of ≦80 microns. The temperature was regulated at 60° C. and *Juglans regia* hull extract was added under controlled stirring and temperature adjusted to 35–40° C. till the whole formulation was uniform.

The formulation was applied on nails of seven human subjects having fungal infection of nail. The infection was cured within ten days but the formulation gave a sloggy effect.

EXAMPLE 3

| | |
|---|---|
| Extract of Juglans regia (Walnut) hulls (in acetone/alcohol/Butanol) | 10% |
| Powdered Vetiveria zizanioides root (granulometry ≦ 80 microns) | 25% |
| Polyethylene glycol | 5% |
| Linseed oil | 5% |
| Lanolin | 10% |
| Amyl acetate | 20% |
| Nitrocellulose | 25% |

*Juglans regia* (walnuts) hulls after separating from the nuts were washed with water and air-dried, powdered and extracted with solvents selected from acetone/alcohol/butanol. The extract was made free of solvent and chilled to remove waxes so that juglone is partially fractionated. Roots of *Vetiveria zizanioides* were washed and cleaned with water air-dried and powdered to ≦80 microns.

Lanolin and amyl acetate were melted, nitrocellulose was added, and the mixture was thoroughly stirred. Polyethylene glycol was added while stirring. Powdered *Vetiveria zizanioides* roots were added and stirring was continued. The mixture was cooled to ambient temperature. *Juglans regia* hulls extract was added and temperature was maintained between 35–40° C. and linseed oil was added under mechanically controlled stirrer until the whole composition was uniform and cooled down to ambient temperature.

The formulation was applied on seven human subjects having fungal infection on nails of hand and feet. The fungitoxic effect was observed after three days and complete recovery was observed after six days after application of the cream twice a day one. Cases of recurrence were not reported.

The Main Advantages of the Present Invention are
1. The fungal infection of the nails is completely cured by the fungitoxic synergistic activity of the fully functional Juglone in *Juglans regia* hulls extract.
2. The formulation allows the synergised Juglone of the extract to go deep down to keratinized layer due to which reoccurrence of the infection is avoided.
3. The synergistic activity in the formulation prevents infection on the new nail growths.
4 The formulation based on natural botanical is eco-friendly with no side effects.
5. The active ingredients from natural botanical material do not produce and sensitizing or irritation on application.
6. The formulation on application does not give a sloggy look but its shining effect is appreciated by the users.
7. Walnut hull is a waste material got while cleaning of walnut is used for extraction, which makes the formulation cheaper.

What is claimed is:

1. An antifungal composition for the treatment of human nails which comprises from 10–15% by weight of extract of walnut hull in acetone or alcohol or butanol wherein the extract of walnut hull has been partially fractionated, 20 to 30% by weight of pulverized roots of *Nardostachys jatamansi* or *Vetiveria zizanioides* or *Catharanthus roseus,* 5–10% by weight of polyols selected from propylene glycol, polyethylene glycol, and ethylene glycol, 5–10% by weight of fixed oil selected from sesame oil, mustard oil, and linseed oil 5–10%, 10–15% by weight of non-ionic emulsifiers selected from stearic acid, lanolin and vegetable wax, 15–20% by weight of thickening agent plasticizer selected from polyvinyl acetate, amyl acetate, and food grade gelatin and 20–25% by weight of base selected from nitrocellulose, kaolin and talc, based upon 100% weight of total antifungal composition.

2. A composition as claimed in claim 1 wherein the pulverised plant material of *Nardostachys jatamansi* or *Vetiveria zizanioides* or *Catharanthus roseus* is ≦80 microns.

3. A composition as claimed in claim 1 wherein the emulsifier is selected from stearic acid, vegetable wax and lanolin in a base of kaolin, nitrocellulose or talc.

4. A process for the preparation of an antifungal composition for the treatment of human nails which comprises from 10–15% by weight of extract of walnut hull in acetone or alcohol or butanol wherein the extract of walnut hull has been partially fractionated, 20 to 30% by weight of pulverized roots of *Nardostachys jatamansi* or *Vetiveria zizanioides* or *Catharanthus roseus,* 5–10% by weight of polyols selected from propylene glycol, polyethylene glycol, and ethylene glycol, 5–10% by weight of fixed oil selected from sesame oil, mustard oil, and linseed oil 5–10%, 10–15% by weight of non-ionic emulsifiers selected from stearic acid, lanolin, and vegetable wax, 15–20% by weight of thickening agent plasticizer selected from polyvinyl acetate, amyl acetate, and food grade gelatin and 20–25% by weight of base selected from nitrocellulose, kaolin and talc, based upon 100% weight of total antifungal composition, said process comprising (a) washing the walnut hulls of *Juglans regia* with water, air drying and extracting the said hulls at ambient temperature with acetone, butanol or alcohols, (b) making the extract solvent free by any known method and partially fractionating the said extract by chilling, (c) washing the roots of *Nardostachys jatamansi* or *Vetiveria zizanioides* or *Catharanthus roseus* with water and air drying and powdering the roots to ≦80 microns to get pulverised material, (d) heating a thickening agent plasticizer selected from polyvinyl acetate, food grade gelatin and amyl acetate at a temperature of up to 80° C., (e) adding a base selected from nitrocellulose, kaolin and talc for filling by stirring, and (f) adding a fixed oil selected from sesame oil, mustard oil, and linseed oil and a polyol selected from propylene glycol, polyethylene glycol, and ethylene glycol to the solution from step (e).

5. A process as claimed in claim 4 wherein the plasticizers are melted at about 80° C. and emulsifier is added followed by the addition of the base and thoroughly stirred.

6. A process as claimed in claim 4 wherein the pulverized root material is added and slowly stirred so that a homogeneous emulsion is formed and extract from walnut hull is added and stirred with a controlled stirring motion at a temperature of 35–40° C.

* * * * *

UNITED STATES PATENT AND TRADEMARK OFFICE
CERTIFICATE OF CORRECTION

Page 1 of 1

PATENT NO. : 6,296,838 B1
DATED : October 2, 2001
INVENTOR(S) : Rattan Lal Bindra et al.

It is certified that error appears in the above-identified patent and that said Letters Patent is hereby corrected as shown below:

<u>Title page,</u>
Item [54] Title, change "ANTI-FUNGAL HERBAL FORMULATION FOR TREATMENT OF HUMANS NAILS FUNGUS AND PROCESS THEREOF" to -- ANTI-FUNGAL HERBAL FORMULATION FOR TREATMENT OF HUMAN NAILS INFECTED WITH FUNGUS AND PROCESS FOR THE PREPARATION THEREOF --.

Signed and Sealed this

Nineteenth Day of March, 2002

*Attest:*

*Attesting Officer*

JAMES E. ROGAN
*Director of the United States Patent and Trademark Office*